United States Patent
Mendes Oliveira E Silva et al.

(10) Patent No.: US 10,591,401 B2
(45) Date of Patent: Mar. 17, 2020

(54) EQUIPMENT FOR THE CHROMATIC DISCRIMINATION AND COUNTING OF ORGANISMS

(71) Applicant: UNIVERSIDADE DE AVEIRO, Aveiro (PT)

(72) Inventors: Miguel Augusto Mendes Oliveira E Silva, Aveiro (PT); Rui Manuel Escadas Ramos Martins, Espinho (PT); Amadeu Mortágua Velho Da Maia Soares, Aveiro (PT); Sizenando Nogueira De Abreu, Gafanha Da Nazare (PT)

(73) Assignee: UNIVERSIDADE DE AVEIRO, Aveiro (PT)

( * ) Notice: Subject to any disclaimer, the term of this patent is extended or adjusted under 35 U.S.C. 154(b) by 0 days.

(21) Appl. No.: 15/522,234

(22) PCT Filed: Oct. 27, 2015

(86) PCT No.: PCT/IB2015/058284
§ 371 (c)(1),
(2) Date: Apr. 26, 2017

(87) PCT Pub. No.: WO2016/067202
PCT Pub. Date: May 6, 2016

(65) Prior Publication Data
US 2017/0322139 A1    Nov. 9, 2017

(30) Foreign Application Priority Data
Oct. 27, 2014 (PT) .......................... 108002

(51) Int. Cl.
*G01N 15/14* (2006.01)
*G01N 21/27* (2006.01)
*G01N 15/00* (2006.01)

(52) U.S. Cl.
CPC ......... *G01N 15/1456* (2013.01); *G01N 15/14* (2013.01); *G01N 15/1434* (2013.01);
(Continued)

(58) Field of Classification Search
CPC .......... G01N 15/1456; G01N 15/1434; G01N 21/27; G01N 2201/068; G01N 2015/0065; G01N 2015/1486
See application file for complete search history.

(56) References Cited

U.S. PATENT DOCUMENTS 6,007,690 A * 12/1999 Nelson ............. G01N 27/44791
 204/450
6,591,003 B2 * 7/2003 Chu .................... G01N 15/147
 382/133

(Continued)

FOREIGN PATENT DOCUMENTS

WO    2014144789 A2    9/2014

*Primary Examiner* — Dominic J Bologna
(74) *Attorney, Agent, or Firm* — Leason Ellis LLP

(57) ABSTRACT

The present disclosure relates to a device for chromatic discrimination and counting of organisms in a liquid medium with application to organisms belonging to the genus *Daphnia, Ceriodaphnia, Artemia*, as well *Collembola*; or similar organisms. The device can be applied in the field of ecotoxicology and involves technologies in the areas of analytical instrumentation, electronics, computer science and biology.

8 Claims, 3 Drawing Sheets

(52) U.S. Cl.
CPC ..... *G01N 21/27* (2013.01); *G01N 2015/0065* (2013.01); *G01N 2015/1486* (2013.01); *G01N 2201/068* (2013.01)

(56) References Cited

U.S. PATENT DOCUMENTS

| | | | | |
|---|---|---|---|---|
| 7,113,266 | B1* | 9/2006 | Wells | G01N 15/1404 |
| | | | | 356/336 |
| 2002/0033939 | A1* | 3/2002 | Hansen | G01N 15/14 |
| | | | | 356/73 |
| 2004/0011975 | A1* | 1/2004 | Nicoli | G01N 15/0227 |
| | | | | 250/574 |
| 2004/0021868 | A1* | 2/2004 | Ortyn | C12Q 1/6816 |
| | | | | 356/419 |
| 2004/0125371 | A1* | 7/2004 | Chang | G01J 3/4406 |
| | | | | 356/318 |
| 2005/0105077 | A1* | 5/2005 | Padmanabhan | G01N 15/1484 |
| | | | | 356/39 |
| 2008/0121026 | A1* | 5/2008 | Verdegan | G01N 15/0205 |
| | | | | 73/61.71 |
| 2012/0211679 | A1* | 8/2012 | Heng | G01N 15/1434 |
| | | | | 250/574 |
| 2013/0050782 | A1* | 2/2013 | Heng | G01N 15/1434 |
| | | | | 358/494 |
| 2013/0334407 | A1* | 12/2013 | Perrault, Jr. | G02B 27/30 |
| | | | | 250/227.11 |
| 2016/0003730 | A1* | 1/2016 | Schreuder | G01N 15/1484 |
| | | | | 250/459.1 |
| 2016/0025761 | A1* | 1/2016 | West | G01N 33/56961 |
| | | | | 506/7 |

\* cited by examiner

EQUIPMENT FOR THE CHROMATIC DISCRIMINATION AND COUNTING OF ORGANISMS

CROSS-REFERENCE TO RELATED PATENT APPLICATIONS

This is a U.S. National Phase Application under 35 U.S.C. § 371 of International Patent Application No PCT/IB2015/058284, filed Oct. 27, 2015, and claims priority to Application No. PT 108002, filed Oct. 27, 2014, which are incorporated by reference their entireties. The International Application was published on May 6, 2016, as International Publication No. WO 2016/067202 A1.

FIELD OF THE INVENTION

The present disclosure relates to a device for chromatic discrimination and counting the organisms in liquid medium with application, but not limited, to organisms belonging to *Daphnia, Ceriodaphnia, Artemia,* and *Collembola*; as well as similar organisms.

The present disclosure can be applied in the field of ecotoxicology and involves technologies in the areas of analytical instrumentation, electronics, computer science and biology.

BACKGROUND OF THE INVENTION

One of the most popular biological assays used internationally to assess the chronic toxicity of chemical compounds and to monitor effluent discharges is the *Daphnia* reproduction test, particularly *Daphnia magna, Daphnia pulex* and *Daphnia similis*, but also with *Ceriodaphnia*. Some tests also use the count of fish eggs as evaluation criteria.

Currently the offspring counting of these organisms is made "naked eye" and backlit by technicians that count and pick every single organism, one by one, from the medium. This process must be repeated for the different treatments—for example different concentrations of chemical compound or effluent—and the various replications of each treatment. Thus, this procedure takes a lot of time and it is under the possibility of human error, and it represents a health risk to the technician, as it requires a high eye effort and exposure due to contact or inhalation of contaminants present in the assay medium.

The chromatic characterization is rarely used in ecotoxicology tests, either acute exposure or using offsprings, being considered a subjective measure and/or too time consuming. This characterization can be done with the naked eye, being performed simultaneously with the counting of organisms, making it subjective, time consuming and subject to human error. Alternatively, it can be achieved using photography of each organism, and visually comparing the intensity of pigment with a gray scale. However, this method is rather time consuming and is also subject to human error. It should be noted that the chromatic characterization may be a very sensitive response parameter from the organisms. For example, in breeding tests, *Daphnia* sp. exposed to different concentrations of a particular chemical compound can produce a similar number of offspring but exhibiting different color patterns. Similarly, for example in acute exposure tests, *Daphnia* sp. exposed to different concentrations of a particular chemical compound may be alive but have different chromatic patterns. The chromatic evaluation can also indicate different feed intake levels, for example in response to different levels of dissolved oxygen in water.

In addition, this device allows the intake assessment in organisms, including *Daphnia* sp. and *Ceriodaphnia* sp., exposed to chemical compounds or contaminated effluents. This evaluation is performed through the chromatic characterization of the medium in which these organisms are at two different time points.

These documents illustrate the technical problem to be solved by this solution.

GENERAL DESCRITION

The present disclosure relates to a device for application in ecotoxicological tests for automatic counting and chromatic characterization of organisms in a liquid medium allowing the differentiation of the organisms and any artefact—such as carapaces of *Daphnia* or other particles—or allowing differentiation between different bodies or between different stages of development of the same organism, through different chromatic characteristics—such as fish eggs fertilized/unfertilized. This device makes a total count of the organisms, individualized and not probabilistic counting, and it allows a chromatic characterization of organisms or particles, setting chromatic patterns for the recognition of these groups by analysis and signal processing.

The present embodiments are useful for counting the organisms, distinguishing organisms from non-organisms according to the chromatic characteristic received, such as in differentiating the *Daphnia* organisms in relation to respective carapaces, or, for example, differentiating fertilized fish eggs from not fertilized eggs. With the various embodiments of the invention, in addition to characterize the sample, it counts all the present organisms, with the elimination of false positives, and with a chromatic characterization of all organisms present. In ecotoxicology tests, all organisms on display count towards the final results of the exposure and the equipment performs a full count of the presence of these organisms, one by one, not by a statistical or probabilistic assessment of distribution or number.

In the present disclosure it is considered that the main organisms are *Daphnia* sp., *Ceriodaphnia* sp., *Collembola*, and *Artemia*, but can be used other organisms such as crustacean, plankton, cnidarians, fish eggs, amphibian eggs or even eggs of reptiles or others.

The present disclosure describes a device for chromatic characterization and counting of organisms, with particular interest in ecotoxicology tests using the organisms referred to in this disclosure, but can also be used for counting and chromatic characterization of other bodies in suspension with similar dimensions.

One aspect of the present disclosure describes a device for chromatic discrimination and counting of organisms in liquid medium, comprising:
- a channel for conducting the sample, wherein the channel has an inner section so that organisms are sequentially driven one by one along the channel;
- a collector for conducting the sample to that channel;
- a light emitter to emit a chromatic signal to that channel;
- a light receiver to capture the chromatic signal from the organism on the that channel;
- an electronic data processor configured to differentiate the organisms counted according to the chromatic signal received.

In one embodiment, the device for chromatic discrimination and counting organisms may comprise a tubular duct, preferably a stylet.

In one embodiment, the device collector for chromatic discrimination and counting of organisms can be a funnel.

In one embodiment, the collector device for chromatic discrimination and counting organisms may be positioned relative to the channel so that the sample is driven by gravity.

In one embodiment of the device for chromatic discrimination and counting the organisms, the chromatic signal, present in that channel, is the chromatic signal reflected, absorbed, refracted and/or self-issued by the organism.

In one embodiment of the device for chromatic discrimination and counting the organisms, the light receiver may be placed 180° from the transmitter to capture the chromatic signal transmittance of this organism in the referred channel.

In one embodiment of the device for chromatic discrimination and counting the organisms, the light receiver may be placed at an angle less than 180° from the emitter to capture the chromatic signal reflection, refraction and/or self-emission of this organism in that channel.

In one embodiment of the device for chromatic discrimination and counting organisms, emitter and light receiver are included in a coupled lens array in the cross section of referred channel.

In one embodiment of the device for chromatic discrimination and counting of organisms, the optical component may comprise fibber optics, lens or filter for colour filtering to highlight the distinction between the colour of the chromatic signal received from organism and non-body, particularly with chromatic filtering using a green colour filter.

In one embodiment of the device for chromatic discrimination and counting of organisms, it can comprise a second light emitter and a second light receiver for chromatic characterization of the sample medium.

In one embodiment of the device for chromatic discrimination and counting of organisms, the second light emitter and second light receiver may be arranged upstream of the first light emitter and the first light receiver.

In one embodiment of the device for chromatic discrimination and counting of organisms may further comprise an integrated display screen or to display the counting.

In one embodiment of the device for chromatic discrimination and counting of organisms may further comprise a data link to send the count data.

Another aspect of the present disclosure comprises a system with two or more chromatic discrimination and organism counting devices described in the present disclosure in which the devices are coupled in parallel for simultaneous processing of samples, or coupled in series for sequential sample processing with different characteristics or coupled in series-parallel combination.

In one embodiment the device comprises: a serialization component (2), an optical component (3), an electronic component (4) and a computational component (5).

In one embodiment of the device, the serialization component serializes all the organisms suspended in the liquid medium through a funnel device (2.1) and gravity flow of the liquid along a stylet (2.2) of inner section adapted to the organism dimensions.

In one embodiment of the device, the optical component comprises one or more light emitters (3.1) and one or more light receivers (3.2), radially distributed around an optical window (3.3) located in a cross section of the stylet, and ensuring the interception of the optical beams by all organisms. The capture signal is made by measuring the transmittance at light receivers placed at 180° from the emitters, and/or measuring the reflection, refraction and/or emission in receivers placed at a 180° lower angle from the emitters. The radial arrangement of the optical beams not only allows redundancy in the counting and/or chromatic characterization in the same spatial plan and temporal moment, but also, intercepting the organism at different angles, minimizes problems arising from asymmetric morphology of organisms such as in *Daphnia magna*.

In one embodiment of the device, the electronic component (4) is responsible for conditioning the electrical signals received in the receptor and subsequent analogue-to-digital conversion.

In one embodiment of the device, the computer component (5) is responsible for processing the digital signals for automatic counting and individualized chromatic characterization of all organisms.

A possible embodiment enables adaptation to the chromatic properties of organisms to assess, by selecting the chromatic characteristics of the light-emitting and/or by selecting the colour characteristics of the light receptor, and/or by placing optical filters in the optical beam.

Another possible embodiment includes various optical components arranged on different levels of the stylet serialization component, which allows redundancy in the counting and/or chromatic characteristics of the device thus improving the accuracy.

Another possible embodiment uses optical fibber in the optical component duct (3.4) for driving and possible filtering the optical signal to the detectors (3.2).

Another possible embodiment is characterized by the fact that the optical component uses lens (3.5) for conditioning the optical beam in order to improve the optical signal and/or to maximize yield of light detectors.

Another possible embodiment is characterized by having transmitters and receivers applied on top of the collector container (2.1), allowing the chromatic characterization of the medium simultaneously with the counting and the chromatic characterization of the organisms. This feature enables the realization of the chromatic characterization of the medium simultaneously with the counting and chromatic characterization of organisms. This feature, for example as an indirect measure of the concentration of algae in the medium solution, is particularly useful in ecotoxicological assays for intake assessment.

Another possible embodiment is characterized by the presentation of the results in real time.

Another possible embodiment is characterized by the display of results in the device itself using seven segment displays or other simple viewer that may be part of the device itself.

Another possible embodiment is characterized by sending the results to a computer support system allowing its remote storage and/or other processing on these results.

Another possible embodiment is characterized by replication in parallel of each counting and chromatic characterization device unit, reducing the processing time for multiple replicas and/or allowing simultaneous processing of samples with different characteristics, such as different concentrations.

The device allows the reprocessing of the same sample, as often as necessary, by collecting and replacement of the sample under study.

Throughout the description and claims, the word "comprise" and variations of the word, are not intending to exclude other technical features, components or steps. Additional objects, advantages and features of the invention will become apparent to those skilled in the art upon examination of the description or may be learned by practice of the invention. The following examples and figures are provided by way of illustration and are not intended to be a limitation of the present invention. Furthermore, the present invention covers all possible combinations of particular and preferred forms of embodiment described herein.

BRIEF DESCRIPTION OF THE FIGURES

For an easier understanding of the solution, the attached figures represent preferred embodiments of the invention, however, the figures do not intend to limit the object of the present disclosure.

Figure 1:
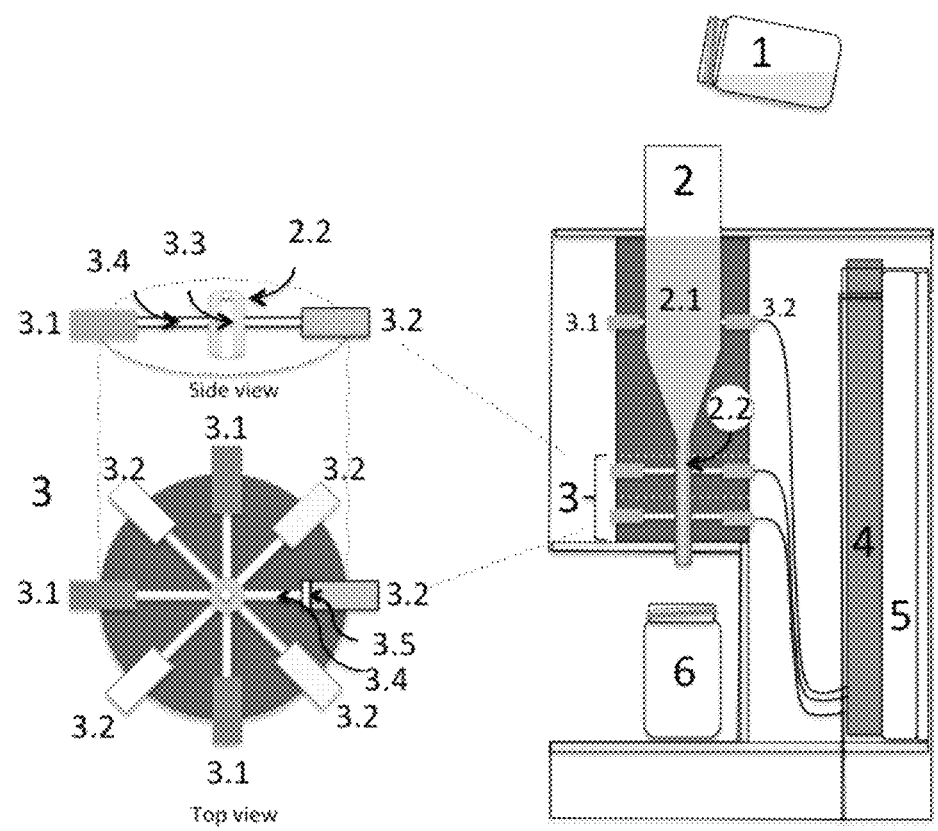
FIG. 1—Schematic representation of an embodiment of the device, illustrating an embodiment of claims 1 to 9, followed by a detailed description of the meaning of constituent parts listed.
Figure 2:
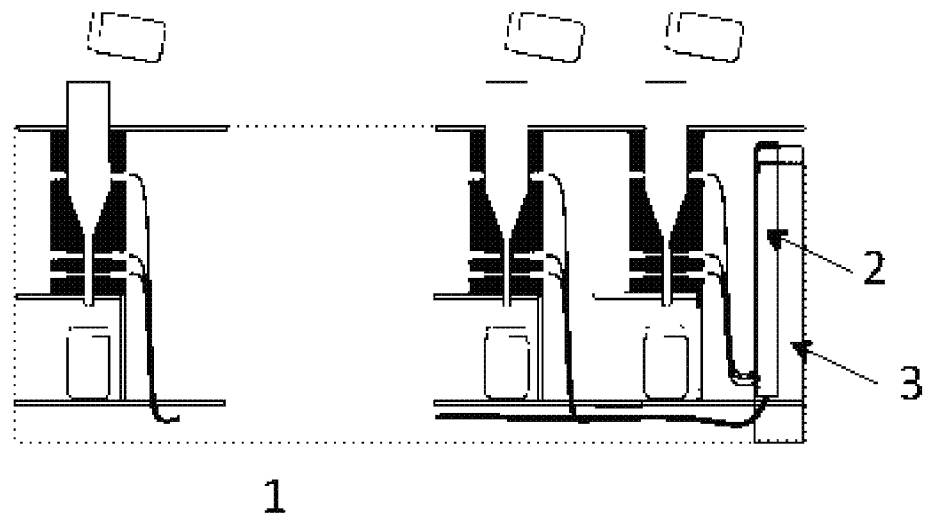
FIG. 2—Representation of an accomplishment for multiple chromatic characterization and counting of several replicates, common procedure in ecotoxicology tests.
Figure 3:
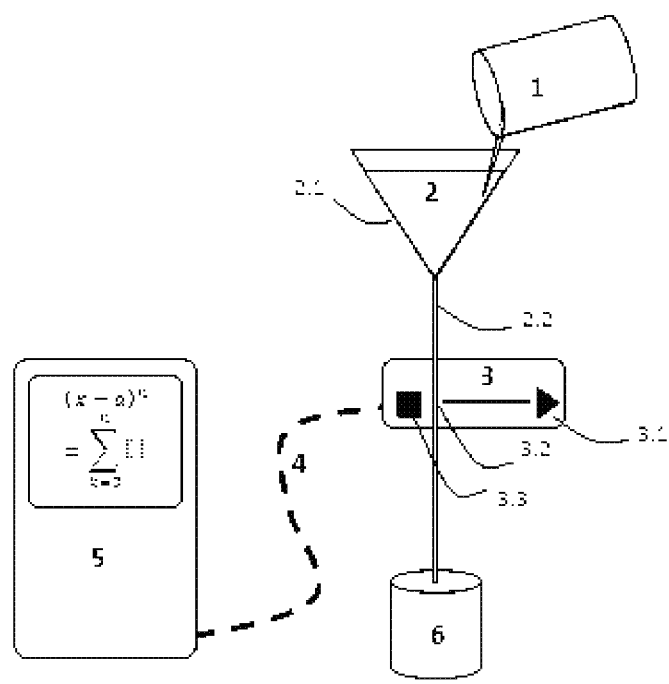
FIG. 3—Schematic representation of a diagram in the form of singular achievement of the counting equipment.
Figure 4:
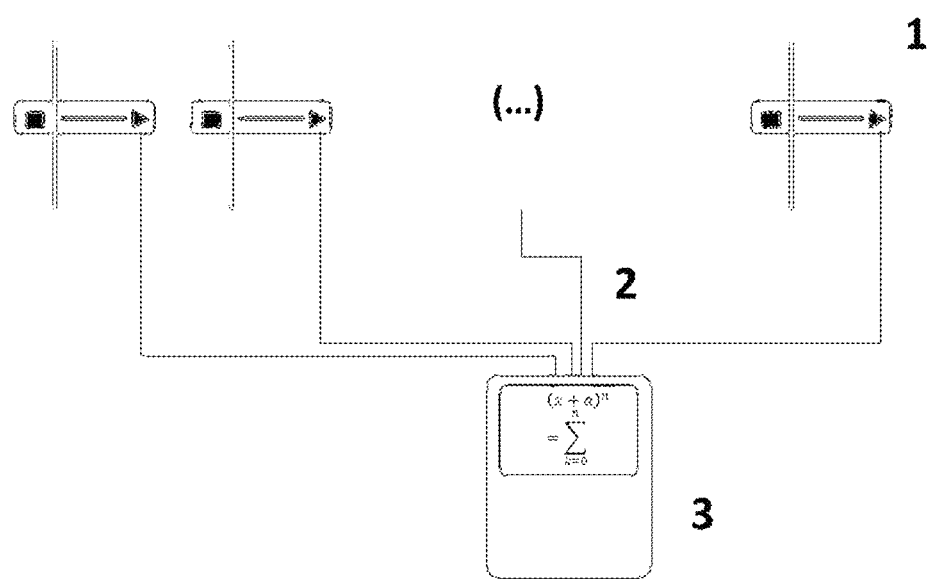
FIG. 4—Schematic representation of an embodiment comprising two or more counting devices connected to a single processing unit.

In ecotoxicology, conducting assay tests with model organisms, eg. *Daphnia* sp., requires the counting of the total number of organisms in various replicates for evaluation of several indexes of toxicity. Currently, the counting is carried out by technicians through direct observation of organisms exposed backlit. However, this counting procedure using "naked eye" is slow, tiresome and prone to human error, as well as may have adverse effects on visual acuity of the technical staff involved in the count. This release automates that counting process with gains in runtime and counting accuracy, and also allows the chromatic characterization of organisms.

The device is intended for counting and chromatic characterization of small-sized bodies in suspension, in particular *Daphnia* sp., *Ceriodaphnia*, *Artemia* or fish eggs, allowing differentiation between specific type of organism to count and any artefacts using different chromatic features. Additionally, this device allows evaluation of ingestion, for example tests on *Daphnia* or *Ceriodaphnia*, by chromatic characterization of the medium in which these organisms are.

In one embodiment, the apparatus has a sampler (1) for organisms in suspension in a liquid. The container in figure is only illustrative of a possible embodiment. The liquid could come from another device, for example, through tubes.

In one embodiment, the serialization component of all organisms present, consists of: a collector of the sample segment (2.1) in the upper section with a funnel-like functionality; and a cylindrical segment, stylet (2.2), in the lower section, with an internal diameter adapted to the size of the bodies. The serialization component, or part thereof, is inserted into a darkroom to eliminate interference from outside light.

In one embodiment, the optical component is composed of one or more light emitters (3.1) and one or more light receivers (3.2), radially distributed around an optical window (3.3) through ducts (3.4) for passage of the beam and it may contain optical fibber. The optical component may also include optical lenses or filters (3.5) placed immediately after the light emitting and/or before the light receivers. The light output is adjustable, eventually with a spectrum adapted to the organism features, ensuring minimal contrast between organisms and the surrounding medium.

In one embodiment, the electronic component performs conditioning of the electrical signals received in the receptors and subsequent analogue-to-digital conversion.

Computer component, portable or otherwise, for counting and/or chromatic characterization of the organisms, may also register other information deemed relevant as the date, location, temperature, etc.

Collector of organisms and solution, may be a container, as illustrated in the figure, or other device This embodiment has the following constituent parts:
Replication of the serialization components;
Electronic component shared;
Computational component shared.

One application for this device can be in ecotoxicology studies with *Daphnia* organisms, particularly in neonates counting as stipulated in the OECD standard number 221, but can be applied in the counting and chromatic characterization of other organisms.

The process is conducted with the serialization of all organisms present, using a device, simultaneously lightweight, space-saving, and with high portability. The device allows the replacement of the current "naked eye" process of organisms counting, namely *Daphnia* in ecotoxicology tests. The device uses an automatic system of high reliability; minimizing duration of counting, human error and possible harmful consequences for the health of technicians. Furthermore, a possible embodiment of this device allows the adaptation to the chromatic features of the medium or the individual organism, minimizing possible counting errors. In addition, the chromatic characterization of the medium can be used as a parameter for evaluating the uptake by organisms, particularly useful in ingestion tests. Regardless of this possibility, with this device, the counting procedure and the counting repetition is a simple and fast process.

Due to the simplicity of the device, it can also be used for automatic counting procedures of other organisms such as *Ceriodaphnia* and *Artemia*, and also fish eggs, differentiating fertilized eggs from unfertilized eggs. In addition to the aquatic organisms counting, this device can be used to count other entities provided they are placed in suspension, such as organisms of the genus *Collembola*.

In addition, chromatic characterization can be used to evaluate the colour of the organisms, an indicator of its health. With the chromatic characterization, this indicator can be translated into a digital quantitative parameter which quantitatively describes the change in the health status resulting from exposure to certain chemicals or environmental factors.

This device also allows the evaluation of ingestion rates, for example in tests on *Daphnia magna* and *Ceriodaphnia* through the chromatic characterization of the medium in which these daphnids are in two different time moments. Description of *Daphnia* Counting in a Sample Containing *Daphnia* Organisms and *Daphnia* Shells Using the Device for Chromatic Discrimination and Counting of Organisms in the Present Disclosure For *Daphnia* neonates counting, the solution with the organisms is placed in the collector of the serialization unit, being the organisms serialized and directed to intercept the beams in the optical component, thereby generating a proper signal to be conditioned and sent to computer unit for processing and result achievement. The total counting, typically a number between 0 and 60 individuals per 100 ml solution, is obtained in about 60 seconds; however, the number of countings per test to be carried out can amount to hundreds. At the beginning of each session, a calibration with a set of the organisms should be made in order to calibrate the equipment according to the organisms in test—*Daphnia* neonates and shells of *Daphnia* neonates. The individual chromatic signal produced by each element of the neonates group shows a similar intra-group pattern but different and distinct from the pattern shown by the elements belonging to the shells of neonates group, and it is based on this chromatic differentiation that the computation unit will discern the group to which belongs each element or item analysed in the optical component, summing up—one by one—the discerned elements to one or to the other group in study, according to the chromatic pattern produced by each element. In routine work, it can be used a "factory" calibration provided with the equipment.

Description of Fertilized Fish Eggs and Unfertilized Fish Eggs Countings Using the Device for Chromatic Discrimination and Counting of the Present Disclosure Organisms In one embodiment for fish egg counting, fertilized and unfertilized eggs are placed in approximately 100 ml of an aqueous solution, or other, and subsequently placed on the collector serialization unit, following the procedure described in the previous paragraph. At the beginning of each session, a calibration should be done with 3 sets of eggs; for example, proceeding with the preparation of a standard consisting in 50 fertilized eggs, another standard with 50 unfertilized eggs, and a mixture, for example, 50 fertilized eggs+50 unfertilized eggs, as an evaluation measure to the equipment. The counting indicates the total number of eggs, the total number of fertilized eggs and the total number of unfertilized eggs, and it may also indicate a number of eggs which classification was inconclusive.

The word "comprises" or "comprising" when used in this document is intended to indicate the presence of features, elements, integers, steps and components mentioned, but does not preclude the presence or addition of one or more other features, elements, integers, steps, components, or groups thereof.

The embodiments described above are combinable with one another.

The invention is of course not in any way restricted to the embodiments described herein and a person of ordinary skill in the area can provide many modification possibilities thereof and replacements of technical features by other equivalent, depending on the requirements of each situation, as defined in the appended claims.

The following claims further define preferred embodiments.

The invention claimed is:

1. A device for chromatic discrimination and counting of organisms in liquid medium sample, comprising:
   a channel for conducting the sample, wherein the channel has an inner section having an internal diameter sized to pass no more than one organism through the inner section at a time so that all the organisms are driven sequentially one-by-one through said channel wherein said channel is a tubular stylet;
   a collector for conducting the sample to that channel wherein said collector is a funnel;
   two or more light emitters to emit a chromatic signal to that channel;
   two or more light receivers to capture the chromatic signal of the organism intercepting that channel;
   wherein light emitters and receivers are radially distributed around an optical window located in a cross section of the stylet;
   wherein the chromatic signal present in the channel is a chromatic signal absorbed, reflected, refracted and/or self-issued by the organisms;
   wherein a first light receiver of the two or more light receivers is at an angle of 180° from a second light emitter of the two or more light emitters to capture the chromatic signal absorbance of the organism;
   wherein further of the two or more light receivers are placed at an angle less than 180° from the first light emitter to capture the chromatic signal reflection, refraction and/or the self-emission of the organism;
   an electronic data processor configured to differentiate the organisms counted according to the chromatic signal received;
   wherein the organisms are neonates of *Daphnia, Ceriodaphnia*, and *Artemia*, fish eggs, and similar sized organisms.

2. The device according to claim 1 wherein the collector is positioned relative to the channel such that the sample is driving by gravity.

3. The device for chromatic discrimination and counting of organisms according to claim 1 further comprising an optical component comprising an-optical fiber, lens or filter for color filtering to highlight the distinction between the color of the chromatic signal received from the organism against non-organism.

4. The device according to claim 1 further comprising one or more light emitters and one or more light receivers for chromatic characterization of the sample medium.

5. The device according to claim 4 wherein the additional light emitters and light receivers are arranged upstream of the first light emitter and light receiver.

6. The device according to claim 1 further comprising a display screen or an integrated counting display.

7. The device according to claim 1 further comprising a data link to send count data.

8. A system comprising two or more devices for discrimination and organism counting according to claim 1 wherein the devices are coupled in parallel for simultaneous processing of samples, or coupled in series for sequentially processing samples with different characteristics, or coupled in combination series-parallel.

* * * * *